United States Patent [19]

Peeters et al.

[11] Patent Number: 4,900,934
[45] Date of Patent: Feb. 13, 1990

[54] APPARATUS FOR SIMULTANEOUS VISUALIZATION AND MEASUREMENT OF FLUORESCENCE FROM FLUORESCENT DYE-TREATED CELL PREPARATIONS AND SOLUTIONS

[75] Inventors: George A. Peeters, Park City; William H. Barry, Salt Lake City, both of Utah

[73] Assignee: University of Utah, Salt Lake City, Utah

[21] Appl. No.: 73,955

[22] Filed: Jul. 15, 1987

[51] Int. Cl.$^4$ .............................................. G01N 21/64
[52] U.S. Cl. .............................. 250/461.2; 250/461.1
[58] Field of Search ........................... 250/461.2, 461.1

[56] References Cited

U.S. PATENT DOCUMENTS

| | | | |
|---|---|---|---|
| 3,497,690 | 2/1970 | Wheeless, Jr. et al. | 250/369 |
| 4,744,667 | 5/1988 | Fay et al. | 250/461.1 |
| 4,745,285 | 5/1988 | Recktenwald et al. | 250/461.2 |

OTHER PUBLICATIONS

Photon Technology International Inc. (PTI) Info-Announcement Re New PTI Deltascan I, Dual-Wavelength Illumination System.
Meridian Instruments, Inc. Literature-(1) Discover the Power of the ACAS 470, (2) ACAS 470 Fluorescence Workstation Bibliography; (3) Automated Selection and Fluorescence Analysis of Cells in Culture.

Primary Examiner—Janice A. Howell
Assistant Examiner—Richard Hanig
Attorney, Agent, or Firm—K. S. Cornaby

[57] ABSTRACT

An apparatus for measuring multiple wavelengths of fluorescence emitted from fluorescent dye-treated cells, tissue preparations, or solutions which is comprised of a custom designed optical module into which is integrally fitted a source of long wavelength red light, a specimen stage, an epifluorescence system, a high intensity ultraviolet light source for excitation, an optical subassembly which permits simultaneous fluorescence detection and real time visualization of the subject under study. A standard microscope may be used in place of the custom designed optical module for integration of the component systems.

9 Claims, 2 Drawing Sheets

APPARATUS FOR SIMULTANEOUS VISUALIZATION AND MEASUREMENT OF FLUORESCENCE FROM FLUORESCENT DYE-TREATED CELL PREPARATIONS AND SOLUTIONS

BACKGROUND OF THE INVENTION

Intracellular ionized free calcium, $[Ca^{2+}]_i$, is well recognized in medical and biological research as an important regulator of normal cell function, and may be an important factor in heart disease, cancer, stroke, neuromuscular disease, and other pathologic conditions. As such, it has been the subject of intense investigation within all fields of cellular physiology. To date, however, it has remained difficult to measure $[Ca^{2+}]_i$ in living cells.

Four general methods of $[Ca^{2+}]_i$ measurement have been used and are currently in use: bioluminescent indicators (eg. aequorin); metallochromic indicators (eg. arsenazo III); fluorescent indicators (eg. quin2); and $Ca^{2+}$-selective microelectrodes. None of these methods have proved completely satisfactory. $Ca^{2+}$-selective microelectrodes have a frequency response too slow to be of use in the measurement of rapid calcium transients, and require impalement of cells which may induce membrane ion leaks. Measurement of $[Ca^{2+}]_i$ with the metallochromic dyes is impeded by difficulty in loading cells, by motion artifacts, by interaction with $Mg^{2+}$ and $H^+$, and by difficulties in calibration. The bioluminescent indicator aequorin has proven more satisfactory than other systems of measurement, but is difficult to calibrate. The $Ca^{2+}$-sensitive fluorescent indicator quin2 may be easily loaded into cells in the acetoxymethyl ester form; however, the free dye released into the cell by intracellular esterase action buffers $[Ca^{2+}]_i$ transients at dye loadings required for sufficient fluorescent intensity. Current systems are limited to fluorescence measurement only and do not provide for real time visualization of the cell or tissue preparation while fluorescence measurement is taking place.

In view of the unsatisfactory results obtained in current methods of $[Ca^{2+}]_i$ measurement, new fluorescent $Ca^{2+}$ indicators have recently been identified as having properties more conducive to such measurement. A discussion of those improved dyes used in conjunction with the present invention follows.

SUMMARY OF THE INVENTION

Fura-2 and indo-1 are new fluorescent $Ca^{2+}$ indicators recently described by Grynkiewicz, et. al. (1985) and Peeters, et. al. (1987). Major advantages of these new indicators over other fluorescent indicators include longer wavelengths for absorption and emission maxima; greater selectivity for $Ca^{2+}$ over other divalent cations such as $Mg^{2+}$, $Mn^{2+}$, $Zn^{2+}$; and a shift in wavelength (for absorption maxima in fura-2, and emission maxima in indo-1) upon binding of $Ca^{2+}$ that allows estimation of $[Ca^{2+}]_i$ independent of total dye concentration or optical path length. In addition, these agents have an increased fluorescence quantum efficiency and a slightly lower affinity for $Ca^{2+}$. These factors would be expected to produce less buffering of calcium transients and thereby make these new fluorescent $Ca^{2+}$ indicators more suitable for measurement of $[Ca^{2+}]_i$ in real time. To take full advantage of these new fluorescent dyes, instrumentation with dual wavelength fluorescence measurement capabilities (for indo-1) and dual wavelength excitation capabilities (for fura-2) is needed.

The present invention is comprised in part of three functional units; a red light source, an ultraviolet light source, and a custom designed optical subassembly for obtaining simultaneous fluorescence intensity measurements and visualization of a preparation from a single collimated light beam. These three units are connected to either a custom microscopic optical housing unit or a commercially available microscope for integration into an optical system. This optical system with associated electronic circuitry uniquely provides for simultaneous measurement of fluorescence intensity at multiple selected wavelengths of light and concurrent, confocal visualization of the preparation under study. The illustrated embodiments herein depict the invention as especially suited for the measurement of $[Ca^{2+}]_i$ with indo-1 by virtue of the combination of optical band pass filters and dichroic mirrors matched to the emission spectra of indo-1 plus calcium. The filters and mirrors are easily accessible, being held within commercially available microscope attachments, and within optical modules designed for the present invention. Changing the band pass filters and dichroic mirrors permits the use of this invention with other fluorescent dyes such as Fura-2, and modifies the system for adaptation to other experimental uses such as the measurement of nanomolar concentrations of Lantham ion in living cells or solutions, or the measurement of hydrogen ion concentration within living cells or solutions.

The optical components of the apparatus herein described occupy no more area than a desk top and, therefore, are conveniently maintained, stored, and moved from location to location. The inherent size of the apparatus and the use of readily available component parts also serve to make the apparatus relatively low in cost and readily affordable.

It is an objective of this invention to provide a unique system for measuring dual wavelength fluorescence such as is required with the use of fluorescent dyes in the measurement of intracellular ionized free calcium, $[Ca^{2+}]_i$.

It is further an objective of this invention to provide a unique system for the visualization of a cell preparation concurrently with measurement of fluorescence therefrom.

It is further an objective of this invention to provide a system for visualization of the subject cell preparation and concurrent measurement of fluorescence which is relatively portable and of low cost.

It is yet another objective of this invention to provide an apparatus for measurement of fluorescence in varying preparations of cellular or tissue types using various fluorescent dyes.

THE DRAWINGS

Preferred embodiments of the invention are illustrated in the attached drawings, in which:

FIG. 1 is a schematic drawing of the apparatus in which the video camera system and fluorescence measurement system are integrated into the system via their connection to a single unit from a camera port of a microscope; and FIG. 2 is a schematic drawing of the apparatus in which the video system is integrated into the apparatus via the observation port of the optical module while the fluorescence measurement system is integrated into the camera port of the optical module.

DETAILED DESCRIPTION OF THE ILLUSTRATED EMBODIMENTS

Figure 1:
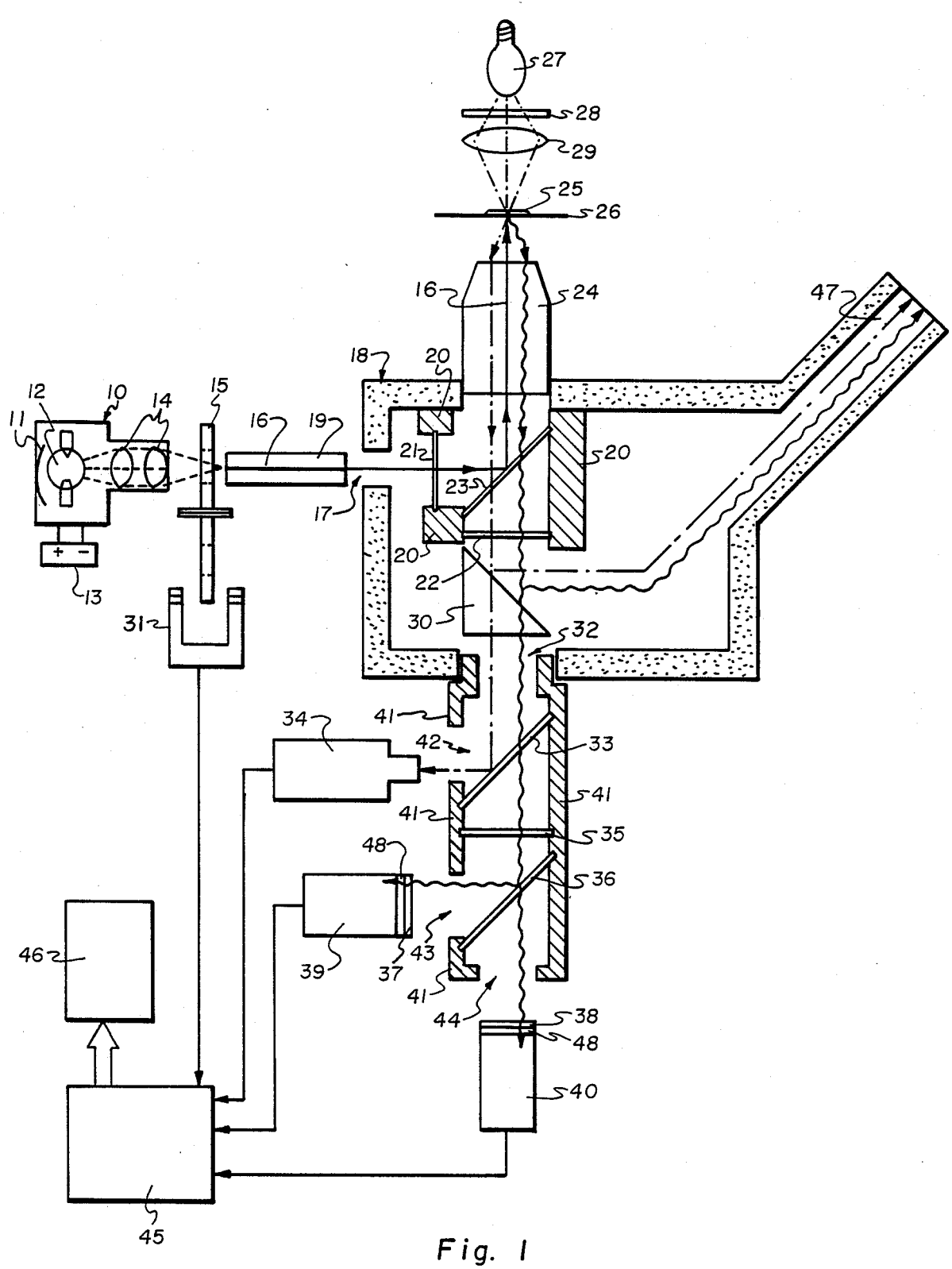

In FIG. 1 the arc lamp assembly, generally at (10), houses the apparatus for providing the source of ultraviolet excitation for the fluorescent dyes. Within the housing are a parabolic reflector (11), a high intensity ultraviolet light source such as a high pressure mercury or xenon arc lamp (12), and a means for high voltage power supply (13). A quartz lens system (14) is added to focus the light into a narrow beam. A high speed chopping wheel (15) containing circular ports capable of carrying optical band pass filters chops the excitation beam. The number and type of optical filters used in the chopping wheel is determined by the fluorescent dye being used. Chopping the excitation beam serves to limit dye bleaching and photodamage to living cells, and facilitates synchronous detection of fluorescence and background signals providing increased immunity from amplifier and photomultiplier tube drift. The excitation beam may be used without chopping to provide maximum frequency response. The position of the rotating ports relative to the light beam is detected by an LED-Photodiode position detector (31) which provides synchronization to electronic circuitry in the instrumentation panel (45). The excitation beam (shown as a solid line at 16) is carried through the epi-fluorescence port (17) of the microscope, generally at 18, via a quartz fiber optic bundle (19).

Within the microscope, a filter block (20) mounted in its standard position holds two band pass filters (21, 22) and a dichroic mirror (23). The excitation band pass filter (21) passes the particular band of wavelengths matched to the absorption peak of the dye being used and is selected to suit the particular dye being used. In point of illustration, a narrow band pass filter centered on 360 nm would be used for indo-1 excitation. It may be desirable in some applications to omit the use of the excitation band pass filter. The dichroic mirror (23) is selected to reflect the shorter excitation wavelengths into the objective lens (24) of the microscope and pass longer wavelengths. The dichroic mirror used for indo-1 would reflect wavelengths shorter than 400 nm. The objective lens (24) focuses the excitation beam, shown as a solid line at 16, onto the dye loaded target cells of the preparation (25), situated upon the specimen stage (26), and collects light from the same focal plane. The collected light contains the fluorescence from the dye and transmitted red light from the red light source, illustrated here as a 12 volt DC lamp (27). Red light emitted from the 12 volt DC lamp passes through a long pass filter (28) which selects red light matched to the peak sensitivity of most available video cameras. The red light replaces standard illumination and is focused by the microscope's condenser (29) onto the dye loaded cells (25) located on the specimen stage (26) of the microscope.

Fluorescence wavelengths (illustrated by the waved line), together with the much longer red wavelengths (illustrated by the intermittently broken line), pass through the dichroic mirror (23) as a single collimated beam. A prism (30) directs 20% of this collimated beam to the binocular head (47) of the microscope, and the remaining 80% is directed to the camera port (32). A long pass barrier filter (22), is used to prevent stray ultraviolet light from reaching the optical paths below the filter block.

A dichroic mirror (33) provides separation of the fluorescence emitted by the dye from the red light, and the red light is deflected thereby into the video camera (34) for imaging of the target cells. The red light directed to the video camera provides the image of the cells under study and provides the optional video motion detector (not shown) with the information necessary to track cell motion.

The short pass filter (35) further isolates the fluorescence signal from unwanted interference from the longer wavelength red light. Separation of the remaining fluorescence into two wavelength bands for measurement and analysis is accomplished by a second dichroic mirror (36) which is specifically selected to separate the wavelengths desired for measurement. With indo-1, a mirror with ½ peak transmission at the isosbestic wavelength of indo-1 is used. Further separation of the fluorescence is accomplished by a band pass filter (37,38) overlying the photocathode of each photomultiplier tube (39,40). An optical shutter (48) is situated between each band pass filter (37,38) and the respective photomultiplier tube.

A black anodized aluminum housing (41) with optical ports, generally at 42, 43, and 44, serves to anchor the dichroic mirrors (33 and 36) and band pass filter (35). Filters (35,37,38) and dichroic mirrors (33,36) are held in removable carriers which form a light-tight seal with the housing (41) and permit easy exchange or replacement. The housing surrounding the photomultiplier tubes (39, 40) contains magnetic shielding, a dynode chain, and a current-to-voltage converting amplifier capable of driving the coaxial cable connecting the photomultiplier tubes to the instrumentation panel (45).

The instrumentation panel (45) contains the pre amplifiers and signal processing electronics needed to synchronously detect the chopped fluorescence signals and subtract background signals. Fluorescence measurements made using the chopped excitation mode are immune to slow changes in detector or amplifier baselines and provide increased protection from photobleaching of dyes and photodamage to living cells. Analog signals representing the fluorescence intensity detected at two wavelengths is received from the photomultiplier tubes and is outputted by the instrumentation panel to a recording device (46) for off-line processing and output to display devices for real time presentation to the operator. The ratio of the two fluorescence intensity signals is also provided to the recording device which can be adapted to record the information by various means such as a strip chart or magnetic tape. Digital conversion and processing, and video motion detection circuitry is available as an optional feature.

Figure 2:
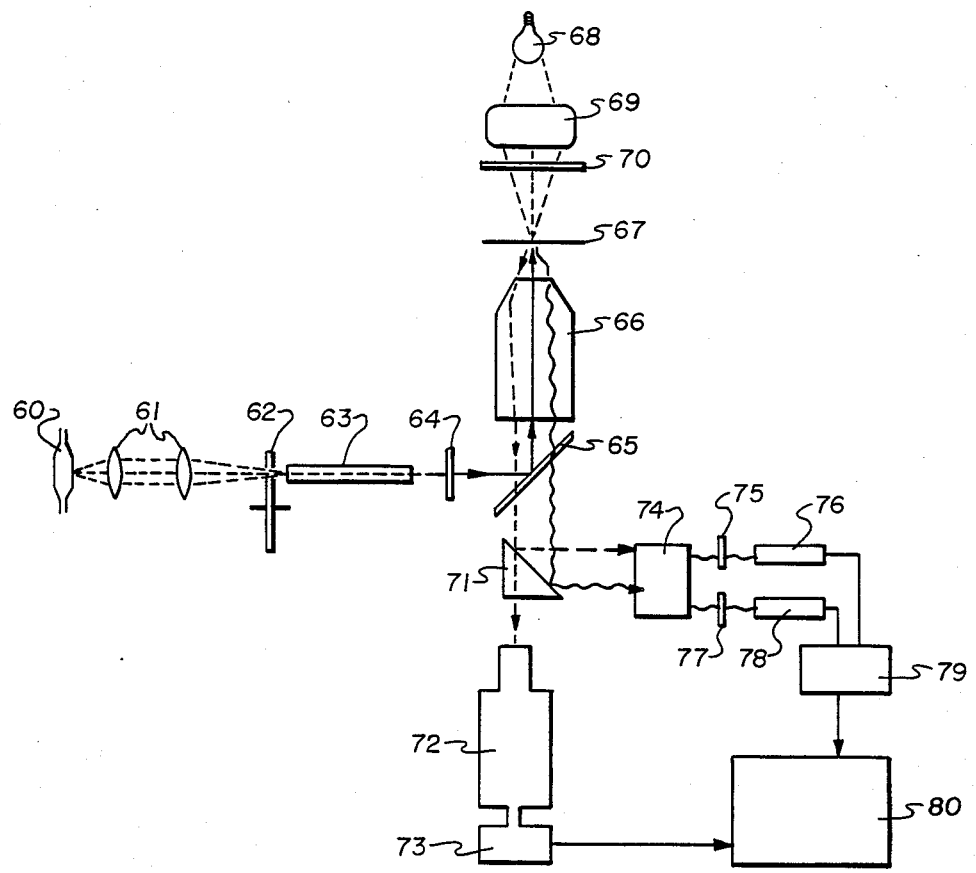

The embodiment of FIG. 2 illustrates many of the same components of the invention embodiment illustrated in FIG. 1, including the arc lamp (60), quartz condensing lenses (61), high speed chopping wheel (62), quartz fiber optic bundle (63), band pass filter (64), dichroic mirror (65), microscope objective (66), specimen stage (67), red light source (68), condenser (69), band pass filter (70), and prism (71). Each of these component parts serve the same function as described above with respect to FIG. 1 and are therefor incorporated by reference herein.

In the embodiment of FIG. 2, the prism (71) is shown to direct 20% of the red light to the video camera (72) which then produces an image of the cells under study, and provides the optional video motion detector (73) with the information necessary to track cell motion. In this embodiment, the video camera system is integrated into the microscope via the observation port of the microscope.

The prism (71) deflects 80% of the fluorescence from the dye and 80% of the red light into a neutral beam splitter (74) which then splits the light into beams of equal wavelength composition. Each separate beam is directed through a separate band pass filter (75, 77) each of which selects for a different wavelength. The individual beams of differing fluorescent wavelength then pass into separate photomultiplier tubes (76, 78). A current-to-voltage converting amplifier within the housing of each photomultiplier tube converts and sends the flourescence signal to an analog circuit processor (79) which then sends the data to the instrument panel (80) for analysis and ultimate recording.

It is notable that varying embodiments are possible to accommodate a variety of experimental needs and formats. The configuration of the housing (41) can be modified to include extra optical ports for the attachment of an extra photomultiplier tube in applications where it is desirable to measure three fluorescent wavelengths. Further, the system of filters and dichroic mirrors within the housing (41) can be extended with more and varying filters and dichroic mirrors for the purpose of further selecting out particular wavelengths. In still other applications, cross polarizing filters can be added adjacent to band pass filters (35, 37, 38) to specially select for non-scattered light.

We claim:

1. An apparatus for measuring fluorescence at multiple wavelengths emitted from fluorescent dye-treated cell or tissue preparations or solutions, comprising in combination:
   an optical housing unit means with at least two access ports therein;
   An epifluorescence system integrally connected to said optical housing unit through one of said access ports therein;
   at least one source of high intensity ultraviolet light for excitation connected to said optical housing unit through one of said access ports therein;
   an optical subassembly means with at least two access ports therein, said optical subassembly being connected to said optical housing unit through one of said access ports therein;
   means for fluorescence detection based within and connected to said optical subassembly through one of said access ports therein;
   means for video monitoring connected to said optical subassembly means through one of said access ports therein; and,
   at least one source of illumination whose wavelength is longer than the excitation wavelength.

2. An apparatus as set forth in claim 1 in which said epifluorescence system comprises, in combination, a means for holding said cell or tissue preparation or solution specimen such as a stage, an objective lens means, and an optical module means for holding and positioning at least one dichroic mirror and at least one filter.

3. An apparatus as set forth in claim 1 in which said means for fluorescence measurement comprises, in combination, a means for holding and positioning at least one dichroic mirror and at least one filter, at least one photomultiplier tube means, and electronic circuitry processing and recording means.

4. An apparatus as set forth in claim 1 in which said means for fluorescence measurement comprises, in combination, a means for holding and positioning at least one dichroic mirror and at least one filter, a means for splitting beams of fluorescent light into multiple beams of light of different wavelength, at least one photomultiplier tube means, and electronic circuitry processing and recording means.

5. An apparatus as set forth in claim 1 in which said optical housing unit is a microscope with at least one access port therein.

6. An apparatus as set forth in claim 1, in which said means for fluorescence detection is capable of detecting at least 2 wavelengths of fluorescence from indo 1.

7. An apparatus as set forth in claim 1, in which at least one source of illumination has wavelengths of greater than 500 nanometers.

8. An apparatus as set forth in claim 1, in which at least one source provides at least two excitation wavelengths for excitation of fura-2.

9. An apparatus for measuring fluorescence at multiple wavelengths emitted from fluorescent dye-treated cell of tissue preparations or solutions, comprising in combination:
   an epifluorescence system;
   at least one source of high intensity ultraviolet light for excitation;
   an optical subassembly means with at least two access ports therein;
   means for fluorescence detection housed within and connected to said optical subassembly through one of said access ports therein;
   means for video monitoring connected to said optical subassembly through one of said access ports therein; and
   at least one source of illumination whose wavelength is longer than the excitation wavelength.

* * * * *